United States Patent
Gübitz et al.

(10) Patent No.: US 8,785,142 B2
(45) Date of Patent: Jul. 22, 2014

(54) TEST ARRANGEMENT

(75) Inventors: Georg Gübitz, Hart bei Graz (AT); Eva Sigl, Groβ Veitsch (AT); Andrea Hasmann, Graz (AT); Marc Schröder, Heinerscheid (LU); Konstantin Schneider, Graz (AT); Alexandra Rollett, Graz (AT); Franz Kaufmann, Freiburg (DE); Andreas Hafner, Gelterkinden BL (CH)

(73) Assignee: Eva Sigl, Gross Veitsch (AT)

( * ) Notice: Subject to any disclaimer, the term of this patent is extended or adjusted under 35 U.S.C. 154(b) by 0 days.

(21) Appl. No.: 13/577,366

(22) PCT Filed: Feb. 9, 2011

(86) PCT No.: PCT/AT2011/000074
§ 371 (c)(1),
(2), (4) Date: Aug. 6, 2012

(87) PCT Pub. No.: WO2011/097664
PCT Pub. Date: Aug. 18, 2011

(65) Prior Publication Data
US 2012/0309036 A1    Dec. 6, 2012

(30) Foreign Application Priority Data
Feb. 10, 2010 (AT) .................................. A 184/2010

(51) Int. Cl.
*G01N 33/573*    (2006.01)

(52) U.S. Cl.
USPC .................. 435/7.4; 435/18; 435/23; 435/25

(58) Field of Classification Search
None
See application file for complete search history.

(56) References Cited

U.S. PATENT DOCUMENTS

| 5,366,881 A | 11/1994 | Singh et al. |
| 2005/0197554 A1* | 9/2005 | Polcha .......................... 600/365 |
| 2006/0233854 A1 | 10/2006 | Seliktar et al. |

FOREIGN PATENT DOCUMENTS

| EP | 0261931 A2 | 3/1988 |
| WO | 89/10566 A1 | 11/1989 |
| WO | 03/033691 A1 | 4/2003 |
| WO | 2007/065423 A1 | 6/2007 |
| WO | 2007/139854 A2 | 12/2007 |

OTHER PUBLICATIONS

Markvicheva et al., "Immobilized Enzymes and Cells in Poly(n-Vinyl Caprolactam)-Based Hydrogels" (2000) Applied Biochemistry and Biotechnology, vol. 88: 145-157.*
Veronese et al. Pegylated enzyme entrapped in poly(vinyl alcohol) hydrogel for biocatalytic application. (2001) II Farmaco, vol. 56: 541-547.*
Thornton et al. "Enzyme-responsive hydrogel particles for the controlled release of proteins." (2008) Soft Matter, 4:821-827.*

(Continued)

*Primary Examiner* — Jon P Weber
*Assistant Examiner* — Teresa E Knight
(74) *Attorney, Agent, or Firm* — Nevrivy Patent Law Group P.L.L.C.

(57) ABSTRACT

The invention relates to an arrangement, comprising a solid carrier and a matrix arranged on the solid carrier, said matrix comprising at least one enzymatically convertible or modifiable molecule and comprising at least one enzyme that can be released by the conversion or modification of the molecule, said enzyme being capable of converting at least one color-changing substrate located in the matrix and/or on the solid carrier.

21 Claims, 4 Drawing Sheets

(56) References Cited

OTHER PUBLICATIONS

Yan et al., Enzyme-containing hydrogel micropatterns serving a dual purpose of cell sequestration and metabolite detection, Biosensors and Bioelectronics, 24: 2604-2610 (2009).

Ulijn et al., Bioresponsive hydrogels, Materials Today, 10: 40-48 (2007).

Kim et al., Micropatterning of proteins on the surface of three-dimensional poly(ethylene glycol) hydrogel microstructures, Analytica Chimica ACTA, 609: 59-65 (2008).

Salinas-Castillo et al., Immobilization of a trienzymatic system in a sol-gel matrix: A new fluorescent biosensor for xanthine, Biosensors and Bioelectronics, 24: 1053-1056 (2008).

Austrian Office Action for Austrian Patent Appl. No. A 184/2010, Austrian Patent Office, Sep. 28, 2010.

International Search Report for International Application No. PCT/AT2011/000074, European Patent Office, Oct. 18, 2011.

Guebitz et al., Enzymes go big: surface hydrolysis and functionalisation of synthetic polymers, Trends in Biotechnology, 26: 32-38 (2007).

Khayat et al., Characterising the size and shape of polyamidoamines in solution as a function of pH using neutron scattering and pulsed-gradient spin-echo NMR, International Journal of Pharmaceutics, 317: 175-186 (2006).

Nagarsekar et al., Genetic synthesis and characterization of pH- and temperature-sensitive silk-elastinlike protein block copolymers, J. Biomed. Mater. Res., 195-203 (2002).

Li et al., Lipid-based nanoparticles for nucleic acid delivery, Pharm Res, 24: 438-449 (2007).

\* cited by examiner

TEST ARRANGEMENT

The present invention relates to an arrangement which is suitable for detecting, inter alia, microorganisms in a sample.

The detection of microorganisms in general and the identification of the detected microorganisms in a sample is of considerable importance in many areas. For example, microorganisms can be responsible for the deterioration or the short shelf life of foodstuffs. Furthermore, microorganisms also play an important role in many diseases (e.g. inflammations) of humans and animals. It is therefore of great importance to detect the presence of microorganisms in good time in order to initiate appropriate measures.

Most diverse systems and methods which are suitable for determining microorganisms in a sample are described in the prior art. These systems can also be used in part to detect special substances (e.g. proteins such as enzymes) in a sample.

Systems which require simple adsorption can be used, for example, to determine microbial contaminations. For example, a gold surface with immobilised carbohydrates or a corresponding derivative is described in US 2001/017270 A1, where the bonding of proteins, viruses or bacteria cells produces a detectable signal.

In other systems, other external influences such as, for example, pH, ionic strength and polarity are used. A change in these parameters caused by the presence of microorganisms can, for example, lead to a colour development or colour change.

In WO 2006/065350 A2, microorganisms are detected by means of a dye which shows a visible colour change in the presence of one or more microorganisms. This colour change is based on differences in the polarity of the solvent or acid-base reactions, redox reactions, which are produced by interaction between microorganisms and sensor.

Another very simple system is based on the detection of a pH shift during the microbial contamination (IE 20060034).

WO 98/010556 A1 discloses, inter alia, a method with the aid of which molecules can be bound at binding sites inside a gel droplet. In this case, molecules which are secreted by cells located inside the gel droplet are bound to the free binding sites of the gel droplets.

WO 03/033691 A1 discloses a microchip with the aid of which the antibacterial activity of antibiotics can be tested. During the manufacture of such a chip, prokaryotic and eukaryotic cells are immobilised in a gel due to the polymerisation thereof.

U.S. Pat. No. 5,366,881 A discloses polymerisable lipids and mixtures thereof in which active substances, enzymes, fluorescent substances and the like can be introduced. The encapsulated substances are released by stimulants from outside such as pH change or ions.

US 2006/0233854 A discloses a matrix consisting of a protein backbone which is cross-linked with ethylene glycol. This matrix is particularly suitable for tissue regeneration. The matrix can additionally comprise a biologically active substance which is released to the surrounding tissue as a result of degradation of the matrix at the target location. In order to test to what extent this matrix releases the biologically active substance contained therein, stained fibrinogen fragments were incorporated in the matrix.

Yan et al. (Biosens Bioelectron. 24(8) (2009): 2604-2610) describes biosensors which are suitable for determining hydrogen peroxide in a sample. These biosensors comprise a polyethylene glycol-based hydrogel which is additionally mixed with horse radish peroxidase. In order to ultimately determine directly the presence of hydrogen peroxide in a sample at the biosensor, a substrate i.e. Amplex Red, was additionally added to the horse radish peroxidase.

Ulijn et al. (Material Today 10(4) (2007): 40-48) is concerned with bioresponsive hydrogels. Most diverse hydrogels are discussed therein, which have different properties depending on the means with which they are brought in contact.

US 2008/0057534 A1 describes the visual detection of a microbial contamination through the degradation of a cover layer consisting of microbe-sensitive dyes. These microbe-sensitive dyes change colour in the presence of microbes in the sample so that the colour is either lost or a colour change takes place. The dyes can be applied to any arbitrary substrate. A certain, albeit very restricted selectivity is possible due to the type of dyes.

In addition to changes in the immediate surroundings, secreted molecules such as, for example, metabolites or enzymes can also be used to detect microorganisms. Thus, for example EP 0 347 771 describes a method for the characterisation of enzymes of various bacteria which frequently occur in blood and other body fluids. Forty six different fluorescent substrates can be used in such a test. Different microorganisms can be identified by this method by using the multiplicity of different fluorescent substrates and enzymatic reaction profiles.

Such systems can be used, for example, in a system such as described in US 2004/0018641 A1. Contamination present in the food sector can be indicated by the appearance or disappearance of computer-readable barcodes. The indication is based on the detection of gases, temperature and pH differences as well as toxins or other metabolites from bacteria.

In addition to the visually apparent dyes, fluorescence can also be used. Very frequently systems based on a PCR method are used here. The system described, for example, in US 2007/0122831 A1 uses the different DNA sequences of different microorganisms for the detection of microbial contamination and for the identification of its origin in aqueous samples.

U.S. Pat. No. 6,297,059 B1 describes a method for the measurement of microbial contamination by means of fluorescence built up on a liquid bilayer membrane. Through the response of multivalent or polyvalent target molecules, two or more fluorescence quenchers or a transmission of extinction energy to a fluorescence acceptor are triggered per molecule and thus a signal amplification is achieved.

Arrangements and devices of the type described above have a number of disadvantages. One of the most significant disadvantages of many of the systems described above is their inertia and low detection sensitivity since the reactions in these devices which are triggered by different substances ("triggers") are not amplified and this only slowly results in a signalling.

Furthermore, in many cases no protective layer is provided so that the system is only stable to a limited extent. Simple display systems based on adsorption or shift of the pH possess very low selectivity and a high sensitivity to external influences. Alternatively to this, systems based on antibodies can be used for this. However, these have the disadvantage of high costs and the need for appropriate instruments.

It is therefore the object of the present invention to provide devices or arrangements which overcome the aforesaid disadvantages of the prior art.

The present invention relates to an arrangement comprising a solid carrier and a matrix arranged on the solid carrier, comprising at least one enzymatically convertible or modifiable molecule, preferably polymer or oligomer, which matrix comprises at least one enzyme that can be released by conversion or modification of the molecule, preferably polymer or oligomer, which enzyme is capable of converting at least one colourproducing/colour-changing substrate located in the matrix and/or on the solid carrier.

The arrangement according to the invention provides a robust system with the aid of which substances present in a sample, in particular enzymes, which for example are secreted by microorganisms or originate from other sources such as, for example, the immune system can be reliably detected.

The arrangement according to the invention comprises, in addition to a solid carrier and an optional opposing semipermeable membrane, a matrix which is arranged on the solid carrier or optionally between the solid carrier and the semipermeable membrane. The matrix comprises at least one molecule, preferably a polymer, which can be degraded, converted or modified by substances (e.g. enzymes) present in the sample. As a result of the degradation, conversion or modification of such molecules or polymers in the matrix, their properties change. In particular, the conversion or modification of the molecule or polymer or oligomer can have the result that their structural properties vary, which can lead to a reduction in the degree of cross-linking or the viscosity, to a change in the pores in the polymer or a degradation of the polymer chains. As a result of these modifications, the releasable enzyme located in the matrix becomes more mobile and can move more freely or diffuse inside the matrix, in particular in the intermediate space between solid carrier and semipermeable membrane. As a result of the increased mobility of the enzyme inside the arrangement, it is possible for this to convert or release a colour-producing substrate located in the matrix and/or on the solid carrier and/or to degrade the molecule or polymer located in the matrix.

By providing enzymes in the matrix according to the invention, which converts, degrades or modifies the molecule or polymer in the matrix, the mobility of the enzyme in the matrix is increased as soon as the molecule or polymer is degraded by extrinsic factors from the sample. This therefore results in a colour reaction and possibly in an amplification of the detection reaction since the release of the molecule or polymermodifying or converting enzyme in the matrix, if present, amplifies and accelerates the degradation of the molecule or polymer. It is thereby possible for the first time to detect the lowest possible concentrations of such substances or microorganisms in a sample.

In addition to enzymes which convert a colour-producing substrate, the matrix or polymer can also contain enzymes which support the modification, conversion or degradation of the polymer. These enzymes are either embedded in the polymer or bound to the polymer via covalent bonds. In the course of the degradation of the polymer, these enzymes are mobilised and can react with the substrate thereof, which is bound to the solid carrier or located in the polymer, and bring about a colour reaction (e.g. formation of colour or change in colour).

Such a system is suitable, for example, to detect the smallest quantities of microorganisms such as, for example, bacteria or fungi, in a sample. An enzyme secreted by a contaminating bacterium or fungus protects the protective, semipermeable membrane, degrades a matrix applied to a carrier material (e.g. a polysaccharide, an enzyme or combinations thereof, with or without cross-linking) and thereby initiates the release of the enzyme which, as an enzymatic amplification system, accelerates the release and/or enables the detection of a microbial contamination for the first time.

There are a plurality of possibilities for degrading the polymer in the matrix, such as, for example, chemical, physical and biochemical. In chemical degradation such as, for example a change in the pH, the ionic strength or chemical reagents, the interactions between the polymer chains amongst one another or of the chains with the solvents on a molecular level are changed. In physical stimulation (e.g. temperature, electromagnetic field and mechanical stress), a change in the molecular interactions takes place. In general, biosensitive polymers and microcapsules can respond simply to pH changes in different environments (Khayat, Int. J. Pharma 2006 317: 175-186; Li and Szoka, Pharmaceutical Res. 2007 24: 438-449; Nagareskar, J. Biomed. Mater. Res. 2002 62: 195-203).

Biosensitive behaviour is imparted to components by a coating with biomaterials which can be degraded by extracellular enzymes. Extracellular microbial enzymes can function as so-called triggers and thus initiate the release of active enzymes included and/or bound in the polymer. In this case, the type of polymer (polypeptide, polysaccharide, synthetic polymer . . . ) defines the type of required trigger enzymes. microorganisms produce a plurality of extracellular enzymes which they release to the environment in order to be able to incorporate these into the cell along with many other functions, e.g. to macerate food constituents. Extracellular enzymes are therefore used inter alia for the degradation of large molecules and polymers. The hydrolysis of a plurality of biopolymers is catalysed by hydrolases which can be divided according to substrate into lipases, proteases, esterases, glycosidases, inter alia.

The term "polypeptide" as used here comprises polypeptides having a minimum size of 50 amino acids and thus also includes proteins.

An "enzyme which can be released by degradation of the polymer" (polypeptide) is an enzyme which is embedded in the polymer of the matrix and as a result of the cross-linking of the polymer, cannot diffuse or which is bound to the polymer by covalent and/or non-covalent bonds. In both cases the enzymes are substantially immobilised in the polymer or only restrictedly mobile prior to degradation of the polymer. Due to the degradation, modification or conversion of the polymer, its long-chain or cross-linked chains are shortened or cleaved so that the enzymes are released, i.e. are more mobile in the matrix and can diffuse around therein.

"Semi-permeable membrane" as used here relates to membranes which allow access of the trigger or enzyme from outside into the arrangement according to the invention but prevents the diffusion of enzymes located in the matrix and other matrix constituents towards the outside.

During the manufacture of the arrangement according to the invention, the enzyme located in the polymer and the colour-producing substrate are selected so that when bringing both substances into contact, the substrate is converted and colour formation thereby comes about.

The colour-producing substrate is converted by enzymes located in the polymer, resulting in a colour formation or colour change. Thus, a colour formation can take place, for example, by cleaving of a chemical group from the substrate molecule or by change in the redox state. The colour formation or change can also take place by enzymatic cleavings in the surrounding matrix (e.g. by cleaving of a quencher, change in the pH by transesterification).

Furthermore, an in-situ dye synthesis or dye discolouration can also take place by enzymatic conversion of one or more substrates, e.g. polymerisation or depolymerisation of a phenol by means of oxidoreductase.

The indicator system can also consist in that the amplifier enzyme is capable of hydrolytically degrading a covering polymer layer and thus allowing the covered colour layer to appear.

The following Table A gives particularly preferred combinations of polymer (and its degrading enzyme), colour-changing enzyme and its substrate:

| Polymer | Degrading trigger enzyme | Included polypeptide (amplifier enzyme) or bound dye | Colour changing substrate |
|---|---|---|---|
| Pectin | Pectinase | PEG-protease | Siloxane-N succinyl ala-ala-pro-leu-p-nitroanilide |
| Pectin | Pectinase | Protease | Siloxane-N succinyl ala-ala-pro-leu-p-nitroanilide |
| Pectin | Pectinase | PVA-protease | Siloxane-N-succinyl ala-ala-pro-leu-p-nitroanilide |
| Pectin | Pectinase | Laccase | Siloxane-ferulic acid |
| Pectin | Pectinase | Laccase | Siloxane-caffeic acid |
| Pectin | Pectinase | Laccase | Siloxane 3,4, dihydrobenzoic acid |
| Pectin | Pectinase | PEG-laccase | Siloxane-ferulic acid |
| Pectin | Pectinase | PEG-laccase | Siloxane-caffeic acid |
| Pectin | Pectinase | PEG-laccase | Siloxane 3,4, dihydrobenzoic acid |
| Pectin | Pectinase | PEG laccase | ABTS |
| Pectin/alginate | Pectinase | PEG-protease | Siloxane-N succinyl ala-ala-pro-leu-p-nitroanilide |
| Pectin/alginate | Pectinase | Protease | Siloxane-N succinyl ala-ala-pro-leu-p-nitroanilide |
| Pectin/alginate | Pectinase | PVA-protease | Siloxane-N succinyl ala-ala-pro-leu-p-nitroanilide |
| Pectin/alginate | Pectinase | Laccase | Siloxane-ferulic acid |
| Pectin/alginate | Pectinase | Laccase | Siloxane-caffeic acid |
| Pectin/alginate | Pectinase | Laccase | Siloxane 3,4, dihydrobenzoic acid |
| Pectin/alginate | Pectinase | PEG-laccase | Siloxane-ferulic acid |
| Pectin/alginate | Pectinase | PEG-laccase | Siloxane-caffeic acid |
| Pectin/alginate | Pectinase | PEG-laccase | Siloxane 3,4, dihydrobenzoic acid |
| Pectin/alginate | Pectinase | PEG-laccase | ABTS |
| Pectin/alginate | Pectinase | Laccase | ABTS |
| Peptidoglycan/alginate | Lysozyme | Laccase | ABTS |
| Peptidoglycan/alginate | Lysozyme | PEG laccase | ABTS |
| Peptidoglycan/alginate | Lysozyme | PEG laccase | Siloxane-ferulic acid |
| Peptidoglycan/alginate | Lysozyme | PEG laccase | Siloxane-caffeic acid |
| Peptidoglycan/alginate | Lysozyme | PEG laccase | Siloxane 3,4, dihydrobenzoic acid |
| Peptidoglycan/alginate | Lysozyme | PEG-protease | Siloxane-N succinyl ala-ala-pro-leu-p-nitroanilide |
| Peptidoglycan/alginate | Lysozyme | Protease | Siloxane-N succinyl ala-ala-pro-leu-p-nitroanilide |
| Peptidoglycan/alginate | Lysozyme | PVA-protease | Siloxane-N succinyl ala-ala-pro-leu-p-nitroanilide |
| Peptidoglycan/agarose | Lysozyme | Laccase | ABTS |
| Peptidoglycan/agarose | Lysozyme | PEG-laccase | ABTS |
| Peptidoglycan/agarose | Lysozyme | PEG laccase | Siloxane-ferulic acid |
| Peptidoglycan/agarose | Lysozyme | PEG laccase | Siloxane-caffeic acid |
| Amylopectin | Amylase | PEG laccase | Siloxane 3,4, dihydrobenzoic acid |
| Peptidoglycan/agarose | Lysozyme | PEG-protease | Siloxane-N succinyl ala-ala-pro-leu-p-nitroanilide |
| Peptidoglycan/agarose | Lysozyme | Protease | Siloxane-N succinyl ala-ala-pro-leu-p nitroanilide |
| Peptidoglycan/agarose | Lysozyme | PVA-protease | Siloxane-N succinyl ala-ala-pro-leu-p-nitroanilide |
| Elastin/agarose | Elastase | PEG-protease | Siloxane-N succinyl ala-ala-pro-leu-p nitroanilide |
| Elastin/agarose | Elastase | Protease | Siloxane-N succinyl ala-ala-pro-leu-p nitroanilide |
| Elastin/agarose | Elastase | PVA-protease | Siloxane-N succinyl ala-ala-pro-leu-p-nitroanilide |
| Elastin/agarose | Elastase | Laccase | Siloxane-ferulic acid |
| Elastin/agarose | Elastase | Laccase | Siloxane-caffeic acid |
| Elastin/agarose | Elastase | Laccase | Siloxane 3,4, dihydrobenzoic acid |
| Elastin/agarose | Elastase | PEG laccase | ABTS |
| Elastin/agarose | Elastase | PEG laccase | Siloxane-ferulic acid |
| Elastin/agarose | Elastase | PEG laccase | Siloxane-caffeic acid |
| Elastin/agarose | Elastase | PEG laccase | Siloxane 3,4, dihydrobenzoic acid |
| Silk/agarose | Elastase | PEG protease | Siloxane-N succinyl ala-ala-pro-leu-p nitroanilide |
| Silk/agarose | Elastase | Protease | Siloxane-N succinyl ala-ala-pro-leu-p-nitroanilide |
| Silk/agarose | Elastase | PVA-protease | Siloxane-N succinyl ala-ala-pro-leu-p-nitroanilide |

| Polymer | Degrading trigger enzyme | Included polypeptide (amplifier enzyme) or bound dye | Colour changing substrate |
|---|---|---|---|
| Silk/agarose | Elastase | Laccase | Siloxane-ferulic acid |
| Silk/agarose | Elastase | Laccase | Siloxane-caffeic acid |
| Silk/agarose | Elastase | Laccase | Siloxane 3,4, dihydrobenzoic acid |
| Silk/agarose | Elastase | PEG-laccase | ABTS |
| Silk/agarose | Elastase | PEG laccase | Siloxane-ferulic acid |
| Silk/agarose | Elastase | PEG laccase | Siloxane-caffeic acid |
| Silk/agarose | Elastase | PEG laccase | Siloxane 3,4, dihydrobenzoic acid |
| Chitosan/agarose | Lysozyme | PEG laccase | ABTS |
| Chitosan/agarose | Lysozyme | PEG laccase | Siloxane-ferulic acid |
| Chitosan/agarose | Lysozyme | PEG laccase | Siloxane-caffeic acid |
| Chitosan/agarose | Amylase | PEG laccase | Siloxane 3,4, dihydrobenzoic acid |
| Chitosan/agarose | Lysozyme | PEG-protease | Siloxane-N succinyl ala-ala-pro-leu-p-nitroanilide |
| Chitosan/agarose | Lysozyme | Protease | Siloxane-N succinyl ala-ala-pro-leu-p-nitroanilide |
| Chitosan/agarose | Lysozyme | PVA-protease | Siloxane-N succinyl ala-ala-pro-leu-p-nitroanilide |
| Gelatine/agarose | Gelatinase | Laccase | ABTS |
| Gelatine/agarose | Gelatinase | PEG laccase | ABTS |
| Gelatine/agarose | Gelatinase | PEG laccase | Siloxane-ferulic acid |
| Gelatine/agarose | Gelatinase | PEG laccase | Siloxane-caffeic acid |
| Gelatine/agarose | Gelatinase | PEG laccase | Siloxane 3,4, dihydrobenzoic acid |
| Gelatine/agarose | Gelatinase | PEG-protease | Siloxane-N succinyl ala-ala-pro-leu-p-nitroanilide |
| Gelatine/agarose | Gelatinase | Protease | Siloxane-N succinyl ala-ala-pro-leu-p-nitroanilide |
| Gelatine/agarose | Gelatinase | PVA-protease | Siloxane-N succinyl ala-ala-pro-leu-p-nitroanilide |
| Gelatine/alginate | Gelatinase | Laccase | ABTS |
| Gelatine/alginate | Gelatinase | PEG laccase | ABTS |
| Gelatine/alginate | Gelatinase | PEG laccase | Siloxane-ferulic acid |
| Gelatine/alginate | Gelatinase | PEG laccase | Siloxane-caffeic acid |
| Gelatine/alginate | Gelatinase | PEG laccase | Siloxane 3,4, dihydrobenzoic acid |
| Gelatine/alginate | Gelatinase | PEG-protease | Siloxane-N succinyl ala-ala-pro-leu-p-nitroanilide |
| Gelatine/alginate | Gelatinase | Protease | Siloxane-N succinyl ala-ala-pro-leu-p-nitroanilide |
| Xylan | Xylanase | Laccase | ABTS |
| Xylan | Xylanase | Xylan | ABTS |
| Xylan | Xylanase | PEG-laccase | Siloxane-ferulic acid |
| Xylan | Xylanase | PEG-laccase | Siloxane-caffeic acid |
| Xylan | Xylanase | PEG-laccase | Siloxane 3,4, dihydrobenzoic acid |
| Xylan | Xylanase | PEG-protease | Siloxane-N succinyl ala-ala-pro-leu-p-nitroanilide |
| Xylan | Xylanase | Protease | Siloxane-N succinyl ala-ala-pro-leu-p-nitroanilide |
| Cellulose | Cellulase | Laccase | ABTS |
| Cellulose | Cellulase | xylan | ABTS |
| Cellulose | Cellulase | PEG laccase | Siloxane-ferulic acid |
| Cellulose | Cellulase | PEG laccase | Siloxane-caffeic acid |
| Cellulose | Cellulase | PEG laccase | Siloxane 3,4, dihydrobenzoic acid |
| Cellulose | Cellulase | PEG-protease | Siloxane-N succinyl ala-ala-pro-leu-p-nitroanilide |
| Cellulose | Cellulase | Protease | Siloxane-N succinyl ala-ala-pro-leu-p-nitroanilide |
| Dextran | Amylase | Laccase | ABTS |
| Dextran | Amylase | Xylan | ABTS |
| Dextran | Amylase | PEG laccase | Siloxane-ferulic acid |
| Dextran | Amylase | PEG laccase | Siloxane-caffeic acid |
| Dextran | Amylase | PEG laccase | Siloxane 3,4, dihydrobenzoic acid |
| Dextran | Amylase | PEG-protease | Siloxane-N succinyl ala-ala-pro-leu-p nitroanilide |
| Dextran | Amylase | Protease | Siloxane-N succinyl ala-ala-pro-leu-p nitroanilide |

Oxidoreductases such as laccases or peroxidases, proteases, lipases, esterases, peptidases etc. can be used as amplifier enzymes for the amplification of the display.

According to a preferred embodiment of the present invention, the matrix is arranged as a layer, in the form of capsules or as a hydrogel on the solid carrier.

The matrix between the solid carrier and the semi-permeable membrane can have different forms. The matrix can, for example, be applied as a layer or capsules. The use of capsules or several layers (at least two, three or four) has the advantage that the capsules and layers can have different compositions. It is therefore possible to provide a type of capsule or a layer which comprise enzymes which are capable of degrading the polymer of the matrix. Other capsules or layers, on the other hand, can comprise enzymes which are capable of converting colour-producing substrates. The polymer composition of the different capsules or layers can also vary.

According to a preferred embodiment of the present invention, the matrix can comprise a degradable, modifiable molecule or polymer which can be degraded or modified by enzymes. Naturally however, it is also possible to use molecules or polymers which can be degraded in the course of a pH change or by variation of the ionic strength.

The enzymatically decomposable, convertible or modifiable or degradable polymer is preferably a polysaccharide, polypeptide, polyester, polyamide or a combination thereof.

The degradable or modifiable polymer can be esterified, for example in order to control the degradation or modification by enzymes present in the sample.

According to a preferred embodiment of the present invention, the polysaccharide is selected from the group consisting of pectin, amylose, amylopectin, agarose, alginate, carrageenan, chitin, chitosan, dextran, glycogen, guar, locust bean gum flour, laevan, pectin, pollulan, tamarind seed flour, xanthan and xylan.

In order to have a further possibility for variation, it is also possible to modify the polymer with functional side chains. These side chains are capable of forming a polymer network which is stable to autohydrolysis by covalent cross-linking. The degradability by the trigger enzymes already described is not influenced thereby. Possibilities for such side chains would be radically polymerising monomers such as acrylates or methacrylates.

Protein-based polymers which can be used according to the invention can be silk and elastin-like protein polymers.

In order to achieve an improved specificity of the polymers, the polymers can be provided with specific sequences (e.g. amino acid or oligosaccharide sequences) which form cleavage sites for specific enzymes. It is thereby possible to produce polymers which are cleaved in contact with the substances (e.g. enzymes) to be detected.

According to a preferred embodiment of the present invention, the degradable polymer is selected from the group consisting of gum arabic, agar, agarose, maltodextrins, alginic acid and salts thereof, in particular sodium alginate or calcium alginate, liposomes, fats, cetyl alcohol, collagen, chitosan, peptidoglycan, leithins, gelatins, albumin, shellac, polysaccharides, in particular starch or dextran, cyclodextrins, pectin, carragenan and wax.

According to a preferred embodiment of the present invention, the polymer-degrading compound is an enzyme.

The enzyme comprised in the matrix is preferably selected from the group consisting of hydrolases and oxidoreductases such as, for example, proteases, laccases or peroxidases.

In order to restrict the mobility of the enzymes in the polymer before its degradation, in order to impede or prevent the premature degradation of the polymer and to prevent the colour-producing substrate from being prematurely converted, the enzyme which can be released by the conversion or modification or degradation of the molecule or polymer can be bound chemically or adsorptively, for example, to polyvinyl alcohol, polyethylene glycol (PEG) or peptides or its molecular weight can be genetically increased by fusion, e.g. with elastin or other peptides or proteins. As a result of the binding of the polypeptide to these high-molecular groups, the diffusion in the polymer is substantially impeded.

According to a preferred embodiment of the present invention, the colour-producing substrate is selected from the group consisting of phenolic compounds and azo dyes such as ferulic acid, caffeic acid, 3,4-dihydroxybenzoic acid, Reactive Blue, Indigo Carmine, ABTS or Guaiacol.

The semi-permeable membrane is preferably selected from the group consisting of cellulose derivatives, polyamides, polyacrylamides and polyester.

A semi-permeable character is achieved by modification of the surface of one side which, for example, is made hydrophilic or hydrophobic. This can be achieved, for example, by chemical, physical (plasma) or enzymatic treatment (e.g. Guebitz, G. M., Cavaco-Paulo, A., 2008. Trends in Biotechnology 26, 32-38).

According to a preferred embodiment of the present invention, the solid carrier comprises a material which is selected from the group consisting of inorganic materials, preferably silica gel, aluminium, silicon or glass, organic materials, preferably polyester, polystyrene, polyamide, polyacrylamide or polyvinyl alcohol or biopolymers, preferably paper.

In order to improve the binding between carrier material and matrix, the carrier material can be chemically modified. In the course of the modification, functional groups are applied to the surface which can then be cross-linked covalently with components of the matrix. As an example, trimethylsilyl methacrylate may be mentioned at this point. As described elsewhere, trimethylsilyl groups with hydroxy groups can form covalent ether bridges on surfaces such as occur in glass and also in other polymers. The methacrylic group can then cross link with methacrylic groups of the matrix.

A further aspect of the present invention relates to the use of an arrangement according to the invention to determine the presence and/or characterisation of cells, preferably microorganisms, in a sample.

The microorganisms to be determined and/or characterised are selected from the group consisting of bacteria and fungi.

According to a further aspect, the arrangement can be used for the detection of at least one enzyme in a sample. A still further aspect of the present invention relates to the use of an arrangement according to the invention for the detection of a wound infection by determining the presence of at least one wound-specific enzyme.

According to the present invention, "wound-specific enzymes" are enzymes which usually occur in wound infections. Example enzymes are those enzymes which are secreted by the microorganisms triggering the infection or those enzymes which are released by the body as a response to an infection.

According to a preferred embodiment of the present invention, the at least one enzyme is selected from the groups of hydrolases consisting of amylase, cellulase, xylanase, mannanase, protease, lysozyme, lipase and esterase, oxidase.

The specific invention is further illustrated in detail with reference to the following figures and examples.

EXAMPLES

Example 1

Production of a Biopolymer A

A 5% solution of pectin, obtained from citrus peel with a degree of esterification of 50-60% was prepared by solubilising in water overnight at 50° C. Alternatively pectin from apple peel having a degree of esterification of 70-75% can also be used.

The polysaccharide was stained beforehand with various dyes such as, for example, alizarin, cibachrome, remazol, Victoria blue or others. To this end 10 g of pectin was suspended in acetone with 5 mM dye, heated overnight under reflux and then washed several times with acetone. The pectin solution was polymerised out dropping into a 200 mM $CaCl_2$ solution and the pectin spheres obtained were washed with water.

Enzymatic degradation of biopolymer A 1 g (moist mass) of biopolymer A was stained with alizarin and incubated in 10 mL buffer (50 mM, pH 6.0) for 24 h at room temperature whilst gently agitating using various commercially available pectinases. The supernatants were then adjusted to pH 14 with 1M NaOH and the adsorption was measured at 550 nm with the aid of a UV/VIS photometer.

Figure 1:
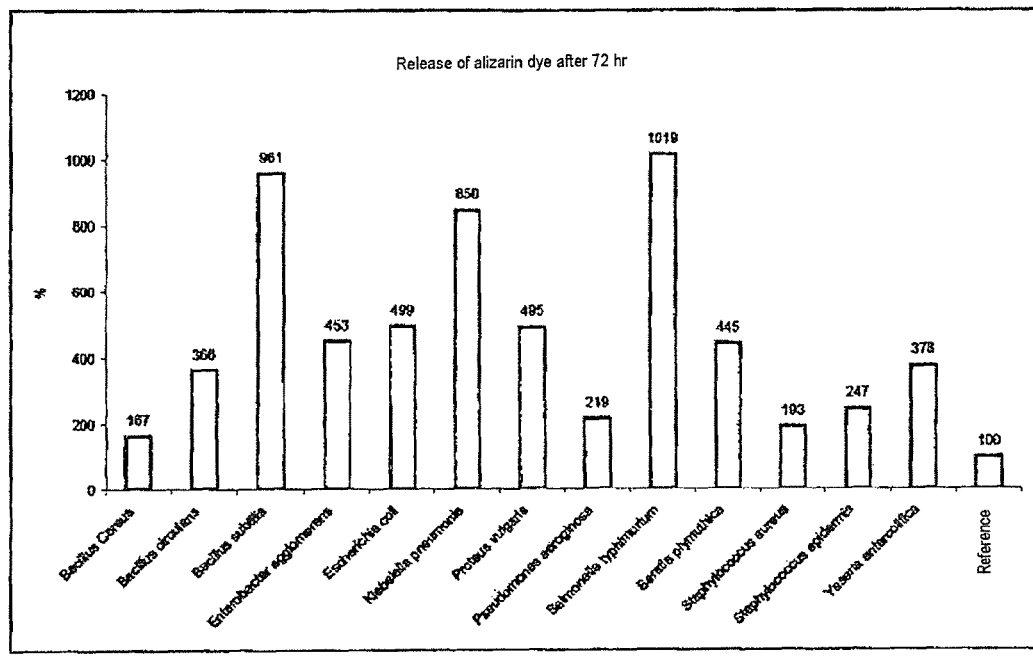
FIG. 1 shows the release of alizarin dye by means of various microorganisms after incubation for 72 hours (Example 3).

Microbiological Degradation of Biopolymer A Various potentially contaminating microorganisms were cultivated by means of preculture. In each case, 1 g of moist mass of biopolymer A stained with alizarin was added to 100 mL of the main culture and inoculated with 100 µL of preculture. Incubation was carried out for 72 hours at 33° C. The biomass was then centrifuged and the absorption of the supernatant was measured at suitable wavelength (FIG. 1).

Example 2

Siloxane Immobilisation of the Substrate for the Amplifier Enzyme

Method A 10 g of silica gel was agitated in 30 mL of 3-9% aminopropyl triethoxysilane in ethanol (95%) for 4 hours at 40° C. The aminated silica gel was then decanted off, washed three times with 70% ethanol and dried to constant weight in the exsiccator.

50 mg of N-(3-dimethylaminopropyl)-N-ethylcarbodiimide hydrochloride, 5 mg (1-hydroxybenzotriazole hydrate) and 50 mg of ferulic acid were dissolved in 20 mL of absolute ethanol. Then 5 g of aminated silica gel was added and stirred for 30 min. After centrifuging the silica gel with the coupled ferulic acid was washed with 70% ethanol and dried to constant weight in the exsiccator. Alternatively to ferulic acid, caffeic acid, 3,4-dihydroxybenzoic acid or Fast Blue RR etc. can be used. Protease substrates such as, for example, N-succinyl-ala-ala-pro-leu-p-nitroanilide, N-succinyl-ala-ala-pro-val-p-nitroanilide or Lleucin-p-nitroanilide can also be immobilised in the same way.

Method B 10 g of silica gel was agitated for 4 hours at 40° C. in 30 mL of a 3-9% mercaptopropyl triethoxysilane in ethanol (95%), washed 3 times with 2-propanol and dried to constant weight in the exsiccator. 155 mg of ferulic acid and 38 mg of dimethylaminopyridine are added to 5 g of pre-treated silica gel suspended in 20 mL of dichloromethane. 165 mg DCC were added to the reaction mixture, cooled to 0° C. with ice and agitated for 3 hours. The temperature was left at room temperature (about 20° C.). The solid modified silica gel was then filtered off, washed three times with dichloromethane and dried overnight in the exsiccator.

Example 3

Production of Biopolymer B

Pectin obtained from citrus peel with a degree of esterification of 50-60% was dissolved overnight in water whilst heating slightly. Alginate in various concentrations (1-20%) was added to the pectin as the main component of the bioresponsive matrix.

Preferably a mixture consisting of 4.5 g pectin and 0.5 g sodium alginate in 100 mL water was used. The gel was produced by dropping the pectin alginate solution into a prepared 200 mM $CaCl_2$ solution. The pectin spheres obtained were washed with water.

Example 4

Incorporation of Enzymes and Proteins in Biopolymer B 5 mL of commercially available protease of *Aspergillus oryzae* was added to a mixture consisting of 4.5 g pectin and 0.5 g sodium alginate in 100 mL water.

After mixing the polysaccharide solution with the enzyme, the polymer was dropped into 200 mM $CaCl_2$ solution and gelled out. The polymer spheres thus obtained were sieved, washed three times with 50 mM tris-HCl buffer pH 7.5 and portioned in respectively 1 g of moist mass in reaction vessels containing 5 mL of 50 mM tris-HCl buffer pH 7.5.

Accordingly, other enzymes such as, for example, laccases of different *trametes* sp. can also be immobilised. Proteins, e.g. casein, collagen etc, can further be incorporated accordingly.

Example 5

Release of Enzymes by Means of Pectinases

Figure 2:
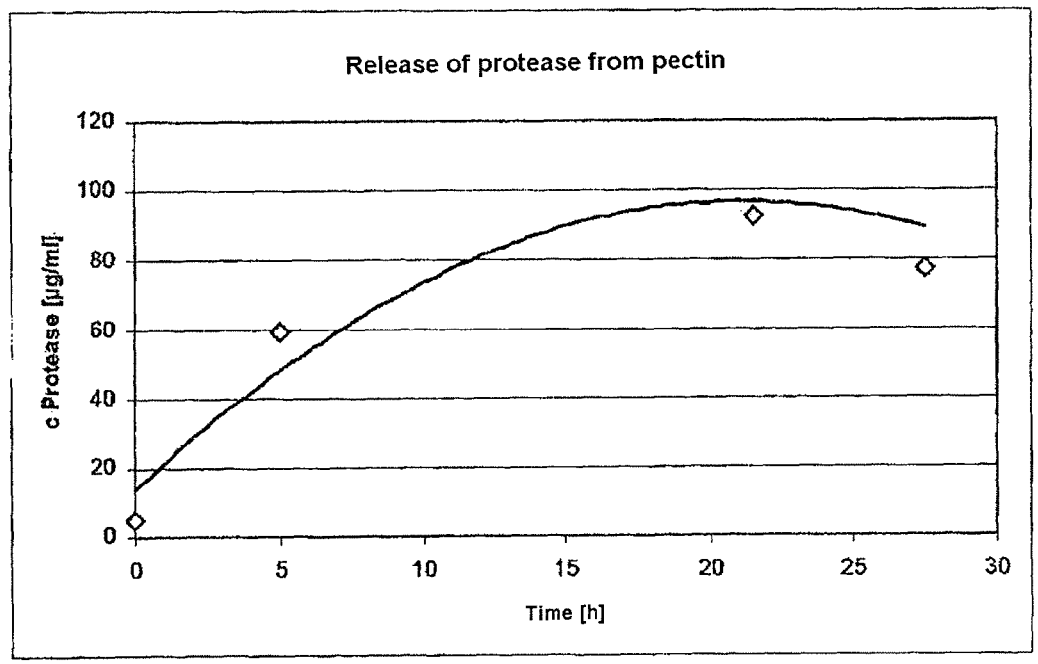
FIG. 2 shows the time behaviour of the release of proteases from the biopolymer by action of pectinases (Example 7).

As a test polymer biopolymer B (example 4) was loaded with a protease of *Aspergillus oryzae*. The polymer spheres thus obtained were sieved, washed three times with 50 mM tris-HCl buffer pH 7.5 and portioned in respectively 1 g of moist mass in reaction vessels containing 5 mL of 50 mM tris-HCl buffer pH 7.5. Enzymatic degradation was started by adding a commercial pectinase. During incubation at room temperature and whilst agitating, samples were taken from the supernatant at specific time intervals. For these samples the protein activities were determined by means of azocasein assay and the protein content was determined (FIG. 2).

Figure 3:
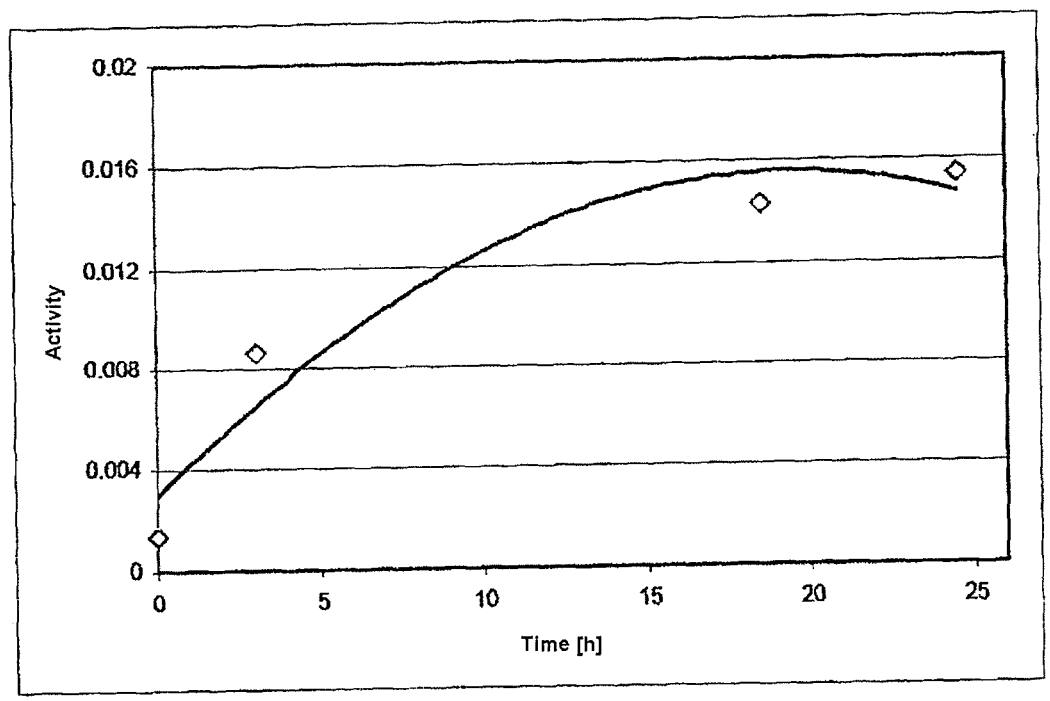
FIG. 3 shows the time behaviour of the release of the amplifier enzyme laccase from the biopolymer by action of a trigger enzyme (pectinases) (Example 7).

Alternatively, the biopolymer can be loaded with any other enzyme such as, for example, from the group of oxidoreductases. Here the activity of the released laccase was then determined accordingly by means of ABTS (FIG. 3).

Example 6

Enzymatic Signalling and Amplification Thereof by Means of Proteases 10 mg of silica gel with immobilised N-succinyl-ala-ala-proleu-p-nitroanilide or L-leucin-p-nitroanilide or N-succinyl-alaala-pro-val-p-nitroanilide as protease substrate (Example 2) were suspended in 1300 µL 50 mM tris-Hl buffer pH 8.3 and incubated with commercially available protease of *aspergillus oryzae* or with wound fluid at room temperature.

Figure 4:
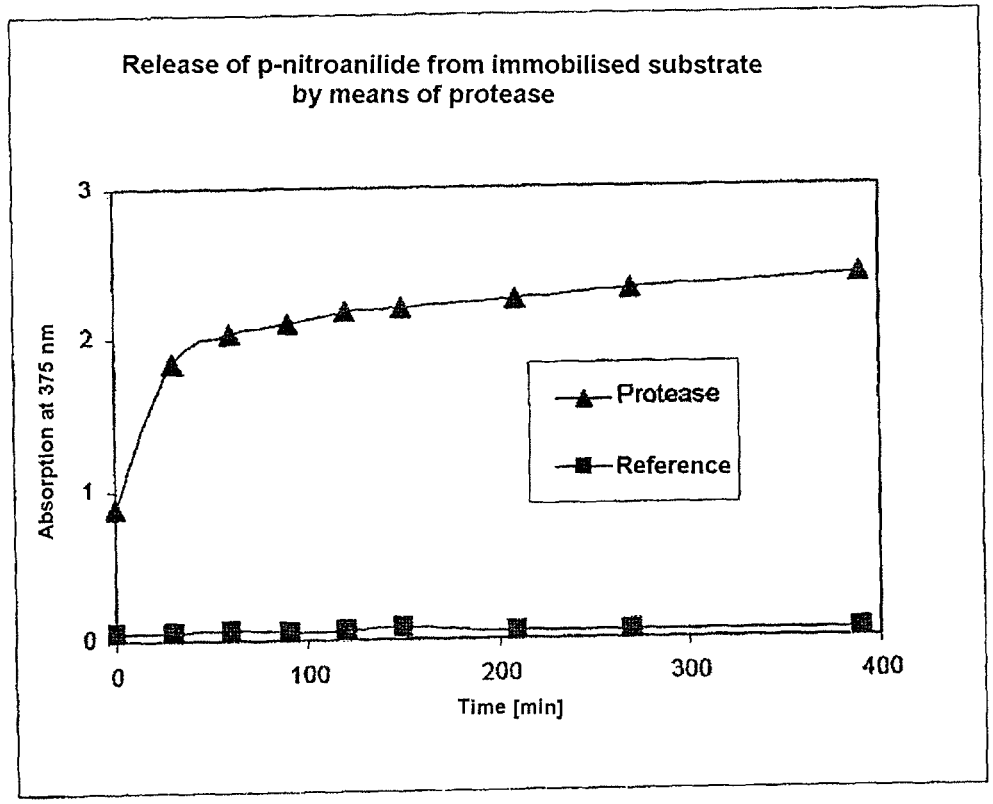
FIG. 4 shows the release of p-nitroanilide of the immobilised substrate by means of commercial protease (Example 8).

The activity was determined by means of UV absorption of the cleaved p-nitroanilide in the supernatant at 375 nm or at 405 nm (FIG. 4).

Example 7

Enzymatic Signalling and Amplification Thereof by Means of Laccases 10 mg of silica gel with immobilised ferulic acid as laccase substrate (Example 2) or with immobilised Fast Blue RR was suspended in 1300 µL 50 mM succinate buffer pH 4.5 and incubated with laccase of *trametes hirsuta* or with wound fluid at room temperature. The activity was determined by means of a colour measurement (yellow-orange) using a spectrophotometer.

Example 8

Enzymatic Signalling and Amplification Thereof by Release of Laccases by Means of Pectinases The biopolymer from Example 4 loaded with laccases of various *Trametes* sp. was used as test polymer.

Figures 5, 6:
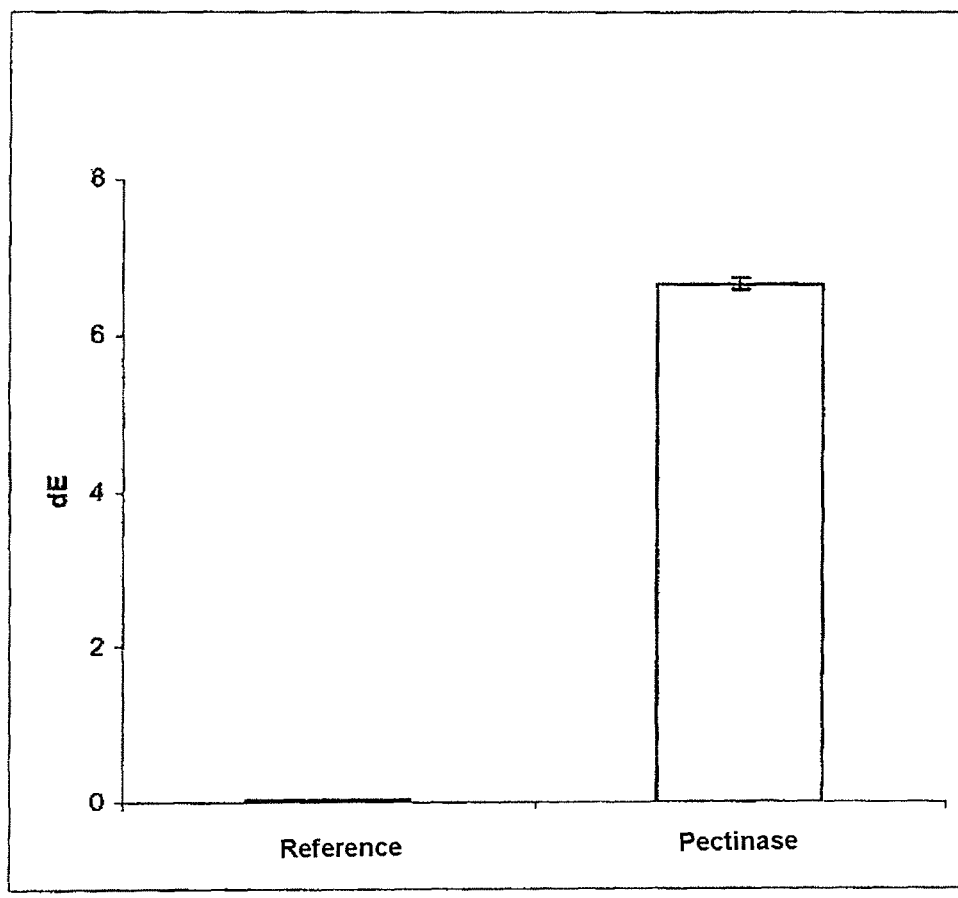
FIG. 5 shows the colour change of immobilised ferulic acid. As a result of the action of the trigger enzyme (pectinase), the amplifier enzyme (laccase) is released from the biopolymer and induces the colour reaction (colouration by oxidation of immobilised ferulic acid) (Example 10).
FIG. 6 shows the conversion of ABTS (diammonium-2,2'-azinobis-(3-ethylbenzthiazolin-6-sulfonic acid)) by laccase as a result of its release from a peptidoglycan matrix following incubation with lysozyme (5000 U/mL) or buffer (control) after various time points.
Figure 7:
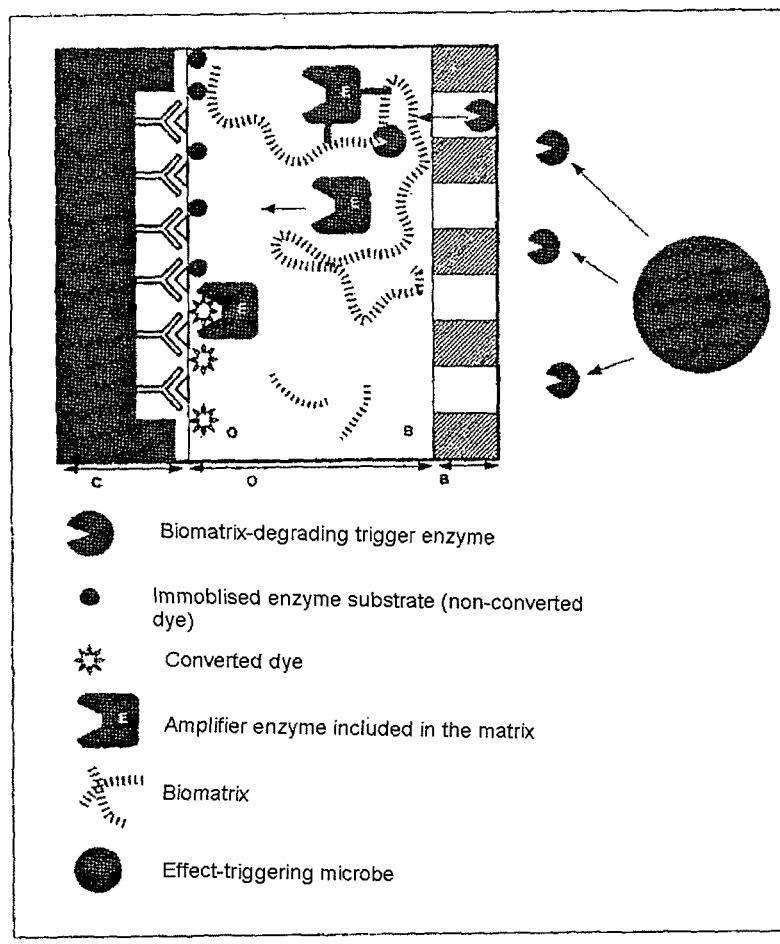
FIG. 7 shows a bioresponsive system according to the invention with enzymatic amplification reaction for controlled release and sensors.

The polymer spheres were sieved, washed three times with 50 mM succinate buffer pH 4.5 and portioned in respectively 1 g moist mass in reaction vessels containing 5 mL of 50 mM succinate buffer pH 4.5 in the presence of 10 mg of silica gel with immobilised ferulic acid as laccase substrate from Example 2. The enzymatic degradation was started by adding commercially available pectinase at room temperature and whilst agitating. After incubation the colour change to yellow-orange was determined by means of a colour measurement using a spectrophotometer (FIG. 5).

Alternatively, the biopolymer can be loaded with a protease of *Aspergillus oryzae*. Here the activity of the released protease is then determined accordingly by means of UV absorption of the cleaved p-nitroanilide in the supernatant at 375 nm.

Example 9

Enzymatic Signalling and Amplification Thereof by Release of Modified Proteases by Means of Pectinases The response behaviour of the bioresponsive polymers can be adjusted by means of the diffusion behaviour both of the trigger and of the amplifier enzymes. By means of a chemical or genetic modification (e.g. enlargement) of the amplifier enzymes, correspondingly lower degrees of cross-linking of the biopolymer can be set with a simultaneous out-diffusion of the amplifier enzyme.

For the chemical modification of amplifier enzymes with water-soluble polymers 1 g of methoxypolyethylene glycol and 0.4 g of cyanuric chloride were dissolved in 100 mL of dry toluene and agitated for 40 hours at 40° C./ The activated polymer was then precipitated in hexane, filtered and dried in vacuum. By using different molecular weights (350, 550, 1100, 2000, 5000 etc.), the diffusion behaviour of the conjugate can be adjusted by means of the length of the polymer. The polymer was attached to the enzyme in weakly basic medium borate buffer pH 9.3. After the reaction, unbound polymer was removed by means of ultrafiltration and the conjugate was used without further purification.

According to Example 6, the biopolymer was loaded with modified protease. The polymer spheres thus obtained were sieved, washed three times with 50 mM succinate buffer pH 4.5 and portioned in respectively 1 g moist mass in reaction vessels containing 5 mL of 50 mM succinate buffer pH 4.5 in the presence of 10 mg of silica gel with immobilised ferulic acid as laccase substrate from Example 2. The enzymatic degradation was started by adding commercially available pectinase at room temperature and whilst agitating. After incubation the colour change to yellow-orange was determined by means of a colour measurement using a spectrophotometer (FIG. 5). Alternatively, the molecular weight of the trigger enzyme can be increased genetically.

Example 10

Enzymatic Signalling and Amplification Thereof by Release of Modified Laccase by Means of Lysozyme A system that can be used in the medical field uses the enzyme lysozyme as a trigger enzyme. This enzyme of the body's own native immune response is formed and secreted in the case of infection. The main task of the enzyme is destruction of bacteria by degradation of peptidoglycan, a component of the bacterial cell wall. It has been shown that increased amounts of enzyme are present in the case of a wound infection. In the following system 3.12 mg of micrococcus lysodeicticus cell wall from Sigma was suspended with 1 mL 1% agarose in phosphate buffer pH 7.00. 100 µl of this suspension was mixed in a microtitre plate with 50 µL of a PEG modified laccase. After curing the polymer is washed with buffer and 100 µl of a lysozyme solution (200-5000 U/mL) is applied. Incubation took place at 37° C. 25 µl of the supernatant was removed every 30 minutes. Laccase activity was detected by means of the ABTS assay (1400 µL saccharose buffer+45 µL 1% $H_2O_2$+30 µL ABTS 40 mM):25 µL supernatant+75 µL ABTS solution). A green colouration occurred after a few minutes incubation with lysozyme by conversion of ABTS by the released laccase (FIG. 6).

Example 11

Cross-Linked Biopolymer and Release of Enzymes by Means of Pectinases or Cellulases 5 g of pectin and/or cellulose derivatives are dissolved in 100 mL of water and coupled with 33 mL of a 97% glycidyl methacrylate solution in the presence of 0.5 mL of 6 M HCl.

PES tissue is modified with trimethylsilyl methacrylate and coated with a matrix modified with glycidyl methacrylate and radically polymerised out and thereby covalently cross-linked.

Extracellular enzymes such as pectinases or cellulases can now overwhelm the PES tissue by diffusion and through degradation of the matrix release functional molecules contained therein such as, for example, enzymes which for their part trigger a colour reaction.

Example 12

Cross-Linked Biopolymer and Release of Enzymes by Release of Modified Enzymes by Means of Elastase Another system which can be used in the medical field uses the enzyme elastase as a trigger enzyme. This enzyme is formed or secreted by some types of bacteria but also by the body's own immune response in the case of infection where almost all types of protein can be cleaved. In the case of wound infection, significantly increased amounts of enzyme could be detected in the wound secretion. This enzyme can thus be used as a marker enzyme for incipient wound infections. In the following system 3.12 mg of chitosan was suspended with 1 mL of 1% agarose in phosphate buffer pH 7.0. The chitosan had been previously activated with GMBs in order to cross link it on both sides via the SH group of a cystein and the peptide sequence ala-ala-pro-val. 100 µl of this suspension was mixed in a microtitre plate with 50 µL of a PEG modified laccase. After curing, the polymer is washed with buffer solution and 100 µl of an elastase solution (2-5 U/mL), or with wound secretion, is applied. Incubation took place at 37° C. Every 10 minutes 25 µl of the supernatant was removed. Laccase activity was detected by means of the ABTS assay (1400 µL of saccharose buffer+45 µL of 1% $H_2O_2$+30 µL of ABTS 40 mM):25 µL of supernatant+75 µL of ABTS solution). A green colouration occurred after incubation for a few minutes with elastase by conversion of ABTS by the released laccase. No colour change was determined without elastase.

The invention claimed is:

1. An arrangement comprising a solid carrier and a matrix arranged on the solid carrier,
the matrix comprising at least one trigger enzyme convertible or modifiable molecule and at least one amplifier enzyme that can be released by conversion or modification of the molecule,
wherein the amplifier enzyme converts at least one colour-changing immobilized substrate located in the matrix and/or on the solid carrier after the amplifier enzyme is released.

2. The arrangement according to claim 1, characterised in that the matrix is arranged as a layer, in the form of capsules or as a hydrogel on the solid carrier.

3. The arrangement according to claim 1, characterised in that the enzymatically convertible or modifiable molecule is a polymer.

4. The arrangement according to claim 3, characterised in that the polymer is a polysaccharide, polypeptide, polyester, polyamide or a combination thereof.

5. The arrangement according to claim 4, characterised in that the polysaccharide is selected from the group consisting of pectin, amylose, amylopectin, agarose, alginate, carrageenan, chitin, chitosan, dextran, glycogen, locust bean gum, levan, pollulan, xanthan and xylan.

6. The arrangement according to claim 3, characterised in that the polymer is selected from the group consisting of, agar, agarose, maltodextrins, alginic acid and salts thereof, sodium alginate, calcium alginate, collagen, chitosan, peptidoglycan, gelatins, albumin, shellac, polysaccharides, starch, dextran, cyclodextrins, pectin, and carragenan.

7. The arrangement according to claim 3, characterised in that the polymer, the amplifier enzyme and the colour-changing substrate are selected from Table A.

8. The arrangement according to claim 1, characterised in that the amplifier enzyme is conjugated to polyvinyl alcohol, polyethylene glycol (PEG), polypeptide, elastin or a peptide.

9. The arrangement according to claim 8, characterised in that the amplifier enzyme is conjugated by means of a polypeptide or peptide to the enzymatically convertible or modifiable molecule, and wherein the trigger enzyme is selected from the group consisting of a microbial enzyme, an enzyme of the immune system and elastase.

10. The arrangement according to claim 1, characterised in that the colour-changing substrate is selected from the group consisting of phenolic compounds and azo dyes.

11. The arrangement according to claim 10, characterised in that the colour-changing substrate can be converted directly by an amplifier enzymes selected from the group consisting of microbial enzymes, laccases, peroxidases, enzymes of the immune system, and myeloperoxidase.

12. The arrangement according to claim 1, characterised in that the arrangement comprises a semi-permeable membrane opposite the solid carrier.

13. The arrangement according to claim 12, characterised in that the semi-permeable membrane is selected from the group consisting of cellulose derivatives, polyamides, polyacrylamides and polyester.

14. The arrangement according to claim 1, characterised in that the solid carrier comprises a material which is selected from the group consisting of inorganic materials, silica gel, aluminium, silicon, glass, organic materials, polyester, polystyrene, polyamide, polyacrylamide, polyvinyl alcohol, biopolymers, and paper.

15. A method of determining the presence of cells of interest in a sample comprising:
applying the sample to the arrangement of claim 1, and
detecting the presence or absence of a change in colour in the colour-changing substrate,
wherein the convertible or modifiable molecule of the arrangement is modified or converted by a trigger enzyme produced by the cells of interest and the presence of a change in colour of the colour-changing substrate indicates that the cells of interest are present in the sample, and the absence of a change in colour of the colour-changing substrate indicates the cells of interest are absent in the sample.

16. The method of claim 15 wherein the cells are microorganisms.

17. The method of claim 16 wherein the microorganisms are selected from the group consisting of bacteria and fungi.

18. A method of detecting at least one trigger enzyme in a sample comprising:
applying the sample to the arrangement of claim 1, and
detecting the presence or absence of a change in colour of the colour-changing substrate,
wherein the convertible or modifiable molecule of the arrangement is modified or converted by the at least one trigger enzyme of interest and the presence of a change in colour of the colour-changing substrate indicates the at least one trigger enzyme of interest is present in the sample, and the absence of a change in colour of the colour-changing substrate indicates the at least one trigger enzyme of interest is absent in the sample.

19. A method of detecting wound infection by determining the presence of at least one wound-specific trigger enzyme in a sample comprising:
applying the sample to the arrangement of claim 1, and
detecting the presence or absence of the colour-changing substrate,
wherein the convertible or modifiable molecule of the arrangement is modified or converted by the at least one wound-specific trigger enzyme and the presence of a change in colour of the colour-changing substrate indicates the at least one wound-specific trigger enzyme is present in the sample, and the absence of a change in colour of the colour-changing substrate indicates the at least one wound-specific trigger enzyme is absent in the sample.

20. The method of claim 19, wherein the at least one wound-specific trigger enzyme is selected from the group consisting of amylase, cellulase, xylanase, mannanase, protease, lysozyme, elastase, collagenase, and cathepsin.

21. The arrangement according to claim 1, wherein the amplifier enzyme is selected from the group consisting of a protease, a laccase, and a peroxidase.

* * * * *